United States Patent
Merkus

(10) Patent No.: US 7,700,588 B2
(45) Date of Patent: Apr. 20, 2010

(54) PHARMACEUTICAL COMPOSITIONS COMPRISING MIDAZOLAM IN A HIGH CONCENTRATION

(76) Inventor: Franciscus Wilhelmus Henricus Maria Merkus, Grootreesdijk 26, 2460 Kasterlee (BE)

(*) Notice: Subject to any disclaimer, the term of this patent is extended or adjusted under 35 U.S.C. 154(b) by 432 days.

(21) Appl. No.: 11/034,474

(22) Filed: Jan. 13, 2005

(65) Prior Publication Data

US 2005/0153956 A1 Jul. 14, 2005

(30) Foreign Application Priority Data

Jan. 14, 2004 (GB) .................................. 0400804.1

(51) Int. Cl.
*A01N 43/62* (2006.01)
*C07D 239/72* (2006.01)

(52) U.S. Cl. .................. 514/221; 540/562; 544/283

(58) Field of Classification Search ................. 514/221; 540/562; 544/283
See application file for complete search history.

(56) References Cited

U.S. PATENT DOCUMENTS

| | | | |
|---|---|---|---|
| 3,812,853 A | 5/1974 | Crain | |
| 4,464,378 A | 8/1984 | Hussain | |
| 4,673,679 A | 6/1987 | Aungst et al. | |
| 4,782,047 A | 11/1988 | Benjamin et al. | |
| 4,863,720 A | 9/1989 | Burghart et al. | |
| 4,889,860 A | 12/1989 | Rzeszotarski et al. | |
| 4,946,069 A | 8/1990 | Fuchs | |
| 4,950,664 A | 8/1990 | Goldberg | |
| 4,973,596 A | 11/1990 | Cohen | |
| 5,132,114 A | 7/1992 | Stanley et al. | |
| 5,166,202 A | 11/1992 | Schweizer | |
| 5,169,029 A | 12/1992 | Behar et al. | |
| 5,225,183 A | 7/1993 | Purewal et al. | |
| 5,307,953 A | 5/1994 | Regan | |
| 5,397,771 A * | 3/1995 | Bechgaard et al. .............. 514/2 |
| 5,474,759 A | 12/1995 | Fassberg et al. | |
| 5,529,787 A | 6/1996 | Merrill et al. | |
| 5,543,434 A | 8/1996 | Weg | |
| 5,577,497 A | 11/1996 | Mecikalski et al. | |
| 5,622,166 A | 4/1997 | Eisele et al. | |
| 5,629,011 A | 5/1997 | Illum | |
| 5,637,314 A | 6/1997 | Sharpe et al. | |
| 5,683,677 A | 11/1997 | Purewal et al. | |
| 5,693,608 A | 12/1997 | Bechgaard et al. | |
| 5,695,743 A | 12/1997 | Purewal et al. | |
| 5,702,725 A | 12/1997 | Merrill et al. | |
| 5,766,573 A | 6/1998 | Purewal et al. | |
| 5,855,907 A | 1/1999 | Peyman | |
| 5,866,143 A | 2/1999 | Elkhoury | |
| 5,948,389 A | 9/1999 | Stein | |
| 5,958,379 A | 9/1999 | Regenold et al. | |
| 6,015,797 A | 1/2000 | Camborde et al. | |
| 6,017,963 A | 1/2000 | Alfonso et al. | |
| 6,193,985 B1 | 2/2001 | Sonne | |
| 6,228,383 B1 | 5/2001 | Hansen et al. | |
| 6,234,366 B1 | 5/2001 | Fuchs | |
| 6,255,502 B1 | 7/2001 | Penkler et al. | |
| 6,274,653 B1 | 8/2001 | Hecht et al. | |
| 6,294,192 B1 | 9/2001 | Patel et al. | |
| 6,383,471 B1 | 5/2002 | Chen et al. | |
| 6,608,073 B1 | 8/2003 | Hussain et al. | |
| 6,610,271 B2 | 8/2003 | Wermeling | |
| 6,699,849 B1 | 3/2004 | Loftsson et al. | |
| 6,720,001 B2 | 4/2004 | Chen et al. | |
| 6,737,043 B2 | 5/2004 | Rabinowitz et al. | |
| 6,936,605 B2 | 8/2005 | March | |
| 2001/0055571 A1 | 12/2001 | Wermeling | |
| 2002/0107265 A1 | 8/2002 | Chen et al. | |
| 2003/0012738 A1 | 1/2003 | Rabinowitz et al. | |
| 2003/0027833 A1 | 2/2003 | Cleary et al. | |
| 2004/0176359 A1 | 9/2004 | Wermeling | |
| 2006/0039869 A1 | 2/2006 | Wermeling et al. | |

FOREIGN PATENT DOCUMENTS

| | | |
|---|---|---|
| CA | 2152684 A1 | 1/1996 |
| EP | 1 323 422 A1 | 2/2003 |
| WO | WO 90/02737 | 3/1990 |
| WO | WO 99/42111 A1 | 8/1999 |
| WO | WO 00/74651 A1 | 12/2000 |
| WO | WO 01/06987 A2 | 2/2001 |
| WO | WO 01/30391 A2 | 5/2001 |
| WO | WO 03/004015 A1 | 1/2003 |

OTHER PUBLICATIONS

Tenk et al., English translation of Dutch article, available at least by Oct. 8, 2002 (7 pgs.).

(Continued)

*Primary Examiner*—Sreeni Padmanabhan
*Assistant Examiner*—Umamaheswari Ramachandran
(74) *Attorney, Agent, or Firm*—Mintz, Levin, Cohn, Ferris, Glovsky and Popeo, P.C.; Ivor R. Elrifi

(57) ABSTRACT

Compositions of midazolam, a benzodiazapine, in concentrations of 35-100 mg/ml are disclosed for the treatment of anxiety, epilepsy and epileptic seizures, invasive surgical procedures and diagnostic procedures and sedation. These compositions are particularly characterized by a solubilizer such an propylene glycol. Preferably, the compositions are aqueous solutions for intranasal administration.

15 Claims, No Drawings

OTHER PUBLICATIONS

Boek et al., "Validation of Animal Experiments on Ciliary Function In Vitro. I. The Influence of Substances Used Clinically", *Acta Otolaryngol (Stockh)*, 119, 1999 (pp. 93-97).

Boek et al., "Validation of Animal Experiments on Ciliary Function In Vitro. II. The Influence of Absorption Enhancers, Preservatives and Physiologic Saline", *Acta Otolaryngol (Stockh)*, 119, 1999 (pp. 98-101).

Boek et al., "Physiologic and Hypertonic Saline Solutions Impair Ciliary Activity in Vitro", *The Laryngoscope*, 109, Mar. 1999 (pp. 396-399).

Fisgin et al., "Effects of Intranasal Midazolam and Rectal Diazepam on Acute Convulsions in Children: Prospective Randomized Study", *Journal of Child Neurology*, vol. 17, No. 2, Feb. 2002 (pp. 123-126).

Fisgin et al., "Nasal Midazolam Effects on Childhood Acute Seizures", *Journal of Child Neurology*, vol. 15, No. 12, Dec. 2000 (pp. 833-835).

Fukuta et al., "The sedative effect of intranasal midazolam administration in the dental treatment of patients with mental disabilities Part 1—The effect of a 0.2 mg/kg dose", *The Journal of Clinical Pediatric Dentistry*, vol. 17, No. 4, 1993 (pp. 231-237).

Hermens et al., "Effects of Absorption Enhancers on Human Nasal Tissue Ciliary Movement in Vitro", *Pharmaceutical Research*, vol. 7, No. 2, 1990 (pp. 144-146).

Hermens et al., "The Influence of Drugs on Nasal Ciliary Movement", *Pharmaceutical Research*, vol. 4, No. 6, 1987 (pp. 445-449).

Ljungman et al., "Midazolam Nasal Spray Reduces Procedural Anxiety in Children", *Pediatrics*, vol. 105, No. 1, Jan. 2000 (pp. 73-78).

Marttin et al., "Acute histopathological effects of benzalkonium chloride and absorption enhancers on rat nasal epithelium in vivo", *International Journal of Pharmaceutics*, 141, 1996 (pp. 151-160).

Marttin et al., "Effects of Absorption Enhancers on Rat Nasal Epithelium in Vivo: Release of Marker Compounds in the Nasal Cavity", *Pharmaceutical Research*, vol. 12, No. 8, 1995 (pp. 1151-1157).

Merkus et al., "The influence of absorption enhancers on intranasal insulin absorption in normal and diabetic subjects", *Journal of Controlled Release*, 41, 1996 (pp. 69-75).

Merkus et al., "Absorption enhancers in nasal drug delivery: efficacy and safety", *Journal of Controlled Release*, 24, 1993 (pp. 201-208).

Primosch et al., "Factors associated with administration route when using midazolam for pediatric conscious sedation", *Journal of Dentistry for Children*, Jul.-Aug. 2001 (pp. 233-238).

Romeijn et al., "The effect of nasal drug formulations on ciliary beating in vitro", *International Journal of Pharmaceutics*, 135, 1996 (pp. 137-145).

Rowe et al. "Handbook of Pharmaceutical Excipients", Fourth Edition (12 pgs.).

Rudy et al., "Bioavailability And Pharmacokinetics Of Intranasal Midazolam", *American Association of Pharmaceutical Scientists*, vol. 4, No. 4, Abstract W4175, 2002 (3 pgs.).

Scheepers et al., "Midazolam via the intranasal route: an effective rescue medication for severe epilepsy in adults with a learning disability", *Seizure*, 7, 1998 (pp. 509-512).

Schipper et al., "Absorption enhancers in nasal insulin delivery and their influence on nasal ciliary functioning", *Journal of Controlled Release*, 21, 1992 (pp. 173-186).

Shao et al., "Cyclodextrins as Nasal Absorption Promoters of Insulin: Mechanistic Evaluations", *Pharmaceutical Research*, vol. 9, No. 9, 1992 (pp. 1157-1163).

Suman, *Expert Opin.Biol. Ther.*, vol. 3, No. 3, Jun. 2003 (pp. 519-523).

Van De Donk et al., "The effects of nasal drops and their additives on human nasal mucociliary clearance", *Rhinoloqy*, 20, (undated) (pp. 127-137).

Vande Donk et al., "The effects of nasal drops on the ciliary beat frequency of chicken embryo tracheas", *Rhinology*, 19, 1981 (pp. 215-230).

Van De Donk et al., "The effects of preservatives on the ciliary beat frequency of chicken embryo tracheas", *Rhinology*, 18, 1980 (pp. 119-133).

Weber et al., "Premedication with nasal s-ketamine and midazolam provides good conditions for induction of anesthesia in preschool children", *Can J Anesth*, vol. 50, No. 5. 2003, (pp. 470-475).

Wermeling et al., "Bioavailability and Pharmacokinetics of Lorazepam after Intranasal, Intravenous, and Intramuscular Administration", *J Clin Pharmacol*, 41, 2001 (pp. 1225-1231).

Bechgaard, Erik, et. al., "Solubilization of Various Benzodiazepines for Intranasal Administration, a Pilot Study." *Pharmaceutical Development and Technology*. 2(3): 293-296 (1997).

Allonen, Hannu, et. al., "Midazolam Kinetics." *Clin. Pharmacol. Ther.* 30:653-661 (1981).

Björkman, S., et. al., "Pharmacokinetics of Midazolam Given as an Intranasal Spray to Adult Surgical Patients." *British Journal of Anaesthesia*. 79:575-580 (1997).

Burstein, Aaron, et. al., "Pharmacokinetics and Pharmacodynamics of Midazolam After Intranasal Administration." *J. Clin. Pharmacol.* 37:711-718 (1997).

Cheng, Andrew. "Intranasal Midazolam for Rapidly Sedating an Adult Patient." *Anesth. Analg.* 76:904 (1993).

Crevoisier, Ch., et. al., "Relationship Between Plasma Concentration and Effect of Midazolam After Oral and Intravenous Administration." *Br. J. clin. Pharmac.* 16:51S-61S (1983).

Davis, Peter, et. al., "Preanesthetic Medication with Intranasal Midazolam for Brief Pediatric Surgical Procedures." *Anesthesiology*. 87:2-5 (1995).

Gerecke, M. "Chemical Structure and Properties of Midazolam Compared With Other Benzodiazepines." *Br. J. clin. Pharmac.* 16:11S-16S (1983).

Gudmundsdottir, H., et. al., "Intranasal Administration of Midazolam in a Cyclodextrin Based Formulation: Bioavailability and Clinical Evaluation in Humans." *Pharmazie*. 56:963-966 (2001).

Heizmann, P., et. al., "Pharmacokinetics and Bioavailability of Midazolam in Man." *Br. J. clin. Pharmac.* 16:43S-49S (1983).

Karl, Helen. et. al., "Comparison of the Safety and Efficacy of Intranasal Midazolam or Sufentanil for Preinduction of Anesthesia in Pediatric Patients." *Anesthesiology*. 76:209-215 (1992).

Kendall, John, et. al., "Intranasal Midazolam in Patients with Status Epilepticus." *Annals of Emergency Medicine*. 29:415-417 (1997).

Knoester, P., et. al., "Midazolam Intranasaal Toegepast, Eventueel Als Noodmedicatie" (in Dutch). *Pharmaceutisch Weekblad*. 137:112-117 (2002a).

Knoester, P., et. al., "Pharmacokinetics and Pharmacodynamics of Midazolam Administered as a Concentrated Nasal Spray. A Study in Healthy Volunteers." *Brit. J. clin. Pharmac*. 53:501-507 (2002).

Kogan, Alexander, et. al., "Premedication with Midazolam in Young Children: A Comparison of Four Routes of Administration." *Paediatric Anaesthesia*. 12:685-689 (2002).

Lahat, Eli, et. al., "Intranasal Midazolam for Childhood Seizures." *The Lancet*. 352:620 (1998).

Lahat, Eli, et. al., "Comparison of Intranasal Midazolam with Intravenous Diazepam for Treating Febrile Seizures in Children: Prospective Randomised Study." *British Medical Journal*. 321:83-86 (2000).

Loftsson, T., et. al., "Cyclodextrin Solubilization of Benzodiazepine Formulation of Midazolam nasal spray." *International Journal of Pharmaceutics*. 212:29-40 (2001).

Lugo, Ralph, et. al., "Complication of Intranasal Midazolam." *Pediatrics*. 92:638 (1993).

Lui, Chung, et. al., "Intranasal Absorption of Flurazepam, Midazolam and Triazolam in Dogs." *Journal of Pharmaceutical Sciences*. 80:1125-1129 (1991).

Malinovsky, J., et. al, "Plasma Concentrations After I.V, Nasal or Rectal Administration in Children." *British Journal of Anaesthesia*. 70:617-620 (1993).

Malinovsky, J., et. al., "Premedication with Midazolam in Children. Effect of Intranasal, Rectal and Oral Routes on Plasma Midazolam Concentrations." Anaesthesia. 50:351-354 (1995).

Marttin, Emmeline, et. al., "Nasal Mucociliary Clearance as a Factor in Nasal Drug Delivery." Advanced Drug Delivery Reviews. 29:13-38 (1998).

Merkus, Paul, et. al., "Classification of Cilio Inhibiting Effects of Nasal Drugs." Laryngoscope. 111:595-602 (2001).

Olivier, J., et. al., "In Situ Nasal Absorption of Midazolam in Rats." International Journal of Pharmaceutics. 213:187-192 (2001).

O'Regan, Mary, et. al., "Nasal Rather Than Rectal Benzodiazepines in the Management of Acute Childhood Seizures?" *Developmental Medicine and Child Neurology*. 38:1037-1045 (1996).

Payne, K., et. al., "The Pharmacokinetics of Midazolam in Paediatric Patients." *Eur. J. Clin. Pharmac*. 37:267-272 (1989).

Persson M. Peter, et. al., "Relation of Sedation and Amnesia to Plasma Concentrations of Midazolam in Surgical Patients." *Clin. Pharmacol. Ther*. 43:324-331 (1988).

Randell, Tarja and Juha Kyttä, "Conscious Sedation in Patients Undergoing Surgical and Investigational Procedures. A Guide to Drug Choice." *CNS Drugs*. *10*:329-342 (1998).

Rey, E., et. al., "Pharmacokinetics of Midazolam in Children: Comparative Study of Intranasal and Intravenous Administration." *European Journal of Clinical Pharmacology*. 41:355-357 (1991).

Saint-Maurice, C., et. al., "The Pharmacokinetics of Rectal Midazolam for Premedication in Children." *Anesthesiology*. 65:536-538 (1986).

Scheepers, Mark, et. al., "Is Intranasal Midazolam an Effective Rescue Medication in Adolescents and Adults with Severe Epilepsy?" *Seizure*. 9:417-422 (2000).

Smith, M.T., et. al., "The Pharmacokinetics of Midazolam in Man." *European Journal of Clinical Pharmacology*. 19:271-278 (1981).

Taylor, M.B., et. al., "Intramuscular Midazolam Premedication in Young Children." *Anaesthesia*. 41:21-26 (1986).

Tenk, H., et. al., "Midazolam Neusspray Bij Patiënten Met Epilepsie." *Pharmaceutisch Weekbad*. 138:99-103 (2003).

Theroux, Mary, et. al., "Efficacy of Intranasal Midazolam in Facilitating Suturing of Lacerations in Preschool Children in the Emergency Department." *Pediatrics*. 91:624-627 (1993).

Tolle-Sander, Sanna, et. al., "Midazolam Exhibits Characteristics of a Highly Permeable P-glycoprotein Substrate." *Pharmaceutical Research*. 20:757-764 (2003).

Uygur-Bayramicli, Oya, et. al, "Sedation with Intranasal Midazolam in Adults Undergoing Upper Gastrointestinal Endoscopy." *Journal of Clinical Gastroenterol*. 35:134-137 (2002).

Walbergh, Eric, et. al., "Plasma Concentrations of Midazolam Following Intranasal Administration." *Anesthesiology*. 74:233-235 (1991).

Wilton, Niall, et. al., "Preanesthetic Sedation of Preschool Children Using Intranasal Midazolam." *Anesthesiology*. 69:972-975 (1988).

Cole, W.H., "Midazolam in Paediatric Anaesthesia." *Anaesth. Intens. Care*. 10:36-39. (1982).

Huang, Chong, et. al., "Mechanism of Nasal Absorption of Drugs I: Physiochemical Parameters Influencing the Rate of In Situ Nasal Absorption of Drugs in Rats." *Journal of Pharmaceutical Sciences*. 74:6 (1985).

Odou, P. "Development of Midazolam Sublingual Tablets: In Vitro Study." Department of Clinical Pharmacy, Faculty of Pharmaceutical and Biological Sciences.

Pujara, Chetan, et. al., "Effects of Formulation Variables on Nasal Epithelial Cell Integrity: Biochemical Evaluations." *International Journal of Pharmaceutics*. 114:197-203 (1995).

Rey, E., "Pharmacokinetics of Midazolam in Children: Comparative Study of Intranasal and Intravenous Administration." *European Journal of Clinical Pharmacology*. 41:355-357 (1991).

Rita, Lucida, et. al., "Intramuscular Midazolam for Pediatric Preanesthetic Sedation: A Double-blind Controlled Study with Morphine." *Anesthesiolog*. 65:53-538 (1986).

Saint-Maurice, C. "The Pharmacokinetics of Rectal Midazolam for Premedication in Children." *Anesthesiology*. 65:53-538 (1986).

Slover, R. "Use of Intranasal Midazolam in Preschool Children." *Anesth. Analg*. 70:S.1-S450 (1990).

Washington, N., et. al., "Determination of Baseline Human Nasal pH and the Effect of Intranasally Administered Buffers." *International Journal of Pharmaceutics*. 198:139-146 (2000).

Wilton, Niall. "Preanesthetic Sedation of Preschool Children Using Intranasal Midazolam." *Anesthesiology*. 69:972-975, (1998).

Zedie, Nishat. "Comparison of Intranasal Midazolam and Sufentanil Premedication in Pediatric Outpatients." Clinical Trials and Therapeutics.

Hirai, Shinichiro, et. al., "Absorption of Drugs from the Nasal Mucosa of Rat." *International Journal of Pharmaceutics*. 7:317-325, (1981).

* cited by examiner

PHARMACEUTICAL COMPOSITIONS COMPRISING MIDAZOLAM IN A HIGH CONCENTRATION

FIELD OF THE INVENTION

The present invention relates to the administration of benzodiazepines such as midazolam. In particular, the invention provides improved midazolam compositions for intranasal administration comprising high concentrations of midazolam.

DISCUSSION OF THE PRIOR ART

Midazolam is a potent benzodiazepine derivative with sedative, anxiolytic, hypnotic, amnesic, anticonvulsant and muscle relaxant pharmacological properties. Because of the basicity of this molecule, it is possible to prepare salts (e.g., with hydrochloric, maleic and lactic acid) which are soluble in water. From these salts, stable aqueous solutions with a pH of 3.5 can be made for intravenous and intramuscular injections of midazolam (Smith et al., 1981; Gerecke, 1983; Persson et al., 1988). Following administration by injection, midazolam is characterized by a fast onset of action as well as short duration of action, due to its rapid metabolic inactivation by liver enzymes. Midazolam is about twice as potent as the classical benzodiazepine diazepam (Randell and Kyttä, 1998).

For drug administration in general, the oral route is probably the most popular route. However, this mode of administration is not suitable for midazolam, as orally delivered midazolam is extensively degraded by first-pass elimination and has also been found to be a substrate for the intestinal drug efflux transporter (Allonen et al., 1981; Crevoisier et al., 1983; Tolle-Sander et al., 2003). The oral absorption of midazolam is therefore relatively low and variable, with absolute bioavailabilies ranging from just 15 to 27% in children (Payne et al., 1989) and from 31 to 72% in healthy adults (Allonen et al., 1981; Heizmann et al., 1983).

Other disadvantages associated with the oral administration of midazolam are the slow onset of action and the observed low peak plasma concentrations. These disadvantages are also observed when midazolam is administered rectally (Saint-Maurice et al., 1986; Malinovsky et al., 1993, 1995).

Rapid onset of the therapeutic action of midazolam can be achieved by intravenous and intramuscular injection (Taylor et al., 1986; Burstein et al., 1997; Uygur-Bayramicli et al., 2002). However, this mode of administration has a number of obvious disadvantages which make it unattractive. For example, injections are painful and not well accepted by the patients, particularly not by young children.

In light of the foregoing, intranasal delivery of midazolam is a very attractive alternative mode of administration.

Intranasal drug administration is painless, results in rapid drug absorption and avoids hepatic first-pass elimination. An additional advantage is the ease of administration, leading to better patient compliance. The mucosa of the nasal cavity is constructed from a highly vascularized tissue covered by a pseudostratified columnar epithelium with numerous microvilli. It has a much higher permeability than other mucosal surfaces, including the sublingual area, various regions of the gastrointestinal tract, and the buccal mucosa. In addition, nasal midazolam administration results in pharmacokinetic and pharmacodynamic profiles, which are very similar to those observed after intravenous injections (Walbergh et al., 1991; Björkman et al., 1997; Burstein et al., 1997).

A number of studies have been reported which demonstrate the beneficial effects of intranasally administered midazolam in patients, both in children and adults. When administered in this way, midazolam appears to have a rapid onset of action (about 10 minutes) and a relatively short duration of action (30 to 60 minutes).

Nasal midazolam at dosages of 0.2 mg/kg has been shown to have sedative and anxiolytic effects in children undergoing various diagnostic and minor surgical procedures, and none of the children had clinical signs of respiratory depression, bradycardia or other side effects (Wilton et al., 1988; Karl et al., 1992; Davis et al., 1995). Comparable clinical results have also been published for nasal midazolam in dosages of 0.3 and 0.4 mg/kg (Theroux et al., 1993; Malinovsky et al., 1995; Kogan et al., 2002). No additional benefit is found for the midazolam dose of 0.3 mg/kg compared to the lower dose of 0.2 mg/kg (Wilton et al., 1988; Davis et al., 1995).

Nasal midazolam (0.2 mg/kg) also suppresses acute seizures and improves the EEG background in epileptic children (O'Regan et al., 1996; Lahat et al., 1998, 2000). As stated by O'Regan et al., (1996): "The EEG technicians welcomed the intranasal administration of benzodiazepines. Their time was no longer wasted in waiting for medical staff to achieve satisfactory intravenous access for the drugs. Often there is a difficulty in siting a butterfly needle or cannula, causing the child to cry, become very restless, or to pull the leads off". Moreover, Lahat et al. (2002) concluded that intranasal midazolam could be provided not only in medical centres but, with appropriate instruction, by the parents of children with febrile seizures at home.

In adult patients undergoing gastrointestinal endoscopy, intranasal administration of midazolam (0.1 mg/kg) is used for the induction of sedation and the nasal route has been shown to cause fewer side effects than intravenous injection (Uygur-Bayramicli et al., 2002). Nasal midazolam is also effective in the short-time management of seizures in adolescent and adult patients with severe epilepsy (Scheepers et al., 2000). In this clinical study the midazolam dosage used was 5 and 10 mg in patients weighing less than 50 kg and more than 50 kg, respectively. Case reports have also shown the sedative effect of midazolam (0.25 mg/kg) in an adult patient with a seizure disorder (Cheng, 1993) and the seizure-terminating activity of nasal midazolam (dose of 4 mg) in an adult epileptic woman (Kendall et al., 1997).

While the above discussed studies have demonstrated the efficacy of nasally administered midazolam, it should be noted that in all clinical studies mentioned above the commercially available injection solutions, containing midazolam at concentrations of 5 mg/ml (Dormicum®, Hoffmann-La Roche, Switzerland), were used. The use of solutions with this concentration of midazolam requires very large volumes of liquid to be applied intranasally, ranging from 1 ml in children to even 4-5 ml in adults.

When such large volumes of liquid are administered intranasally, a large portion of the volume actually drops out of the nose and/or will be swallowed, resulting, at best, in part of the dose being administered orally rather than nasally. This oral midazolam absorption is clearly shown by Burstein et al. (1997). As discussed above, the orally administered midazolam will have a significantly reduced therapeutic effect compared to the intranasally administered midazolam.

The nasal administration of such large volumes of solution also accounts for a number of unpleasant side-effects sometimes experienced by patients, including lacrimation, burning sensations, irritation in the nose and throat, and general discomfort (Lugo et al., 1993; Burstein et al., 1997; Kogan 2002). In addition, treatment failure can occur due to the inadequate technique of delivering unphysiologically large volumes of the midazolam solution (Scheepers et al., 2000).

A further problem is clearly the loss of a large proportion of the composition and of the midazolam, which leads to inconsistent and unpredictable amounts of midazolam being absorbed.

It is therefore clear that the use of commercially available midazolam injection solutions for intranasal midazolam administration is inefficient and unpleasant for the patients, due to the necessary large volumes applied. This can lead to reduced nasal bioavailability and ineffective plasma peak concentrations of midazolam and therefore to an insufficient therapeutic efficacy.

For efficient and comfortable nasal drug delivery, volumes of about 200 µl (100 µl into each nostril) are normally the maximum that should be administered to a patient. This implies that there is an urgent need for the availability of nasal formulations with highly increased midazolam concentrations in comparison with the midazolam injection solutions.

A few nasal midazolam formulations have been developed which seek to reduce the total volume of liquid to be delivered intranasally to the patients. These formulations are described in detail in Table 1 below.

TABLE 1

Nasal Midazolam Formulations

| Reference | Composition | pH |
|---|---|---|
| Lui et al. (1991) | Midazolam HCl 11.1 mg/ml<br>Methocel 1.5% (w/v)<br>Water | about 4 |
| Loftsson et al. (2001) | Midazolam base 17 mg/ml<br>SBEβCD 14% (w/v)<br>HPMC 0.10% (w/v)<br>Benzalkonium chloride 0.02% (w/v)<br>EDTA 0.1% (w/v)<br>Phosphoric acid 0.43% (v/v)<br>Water | 4.3 |
| Knoester et al. (2002a) | Midazolam HCl 30.9 mg/ml<br>Benzyl alcohol 1% (v/v) = 10.46 mg/ml<br>Propylene glycol 25% (v/v) = 259 mg/ml<br>Water | 4 |

HPMC, hydroxypropyl methylcellulose 4000
SBEβCD, sulfobutylether-β-cyclodextrin sodium salt (Captisol ®)

The midazolam formulation used in Lui et al. (1991) is an acidic solution of midazolam hydrochloride (11.1 mg/ml) and 1.5% methocel as a viscosity-enhancing agent. It is prepared by freeze-drying the commercially available midazolam injection solution. The dried product is dissolved in water and mixed with the appropriate volume of a 7.5% methocel aqueous solution.

The formulation has been tested for nasal midazolam absorption in dogs, and not in human subjects. However, nasal administration of a total volume of 200 µl of this formulation will not achieve therapeutically effective midazolam plasma levels in humans, because the midazolam concentration in this formulation is far too low.

The nasal formulation used by Loftsson et al. (2001) comprises midazolam hydrochloride (17 mg/ml) with 14% sulfobutylether-β-cyclodextrin sodium salt (SBEβCD; Captisol®) as solubilizer in an acidic solution at pH 4.3. The presence of 0.1% hydroxypropyl methylcellulose (HPMC) has an additional solubilizing effect. This formulation also contains 0.02% benzalkonium chloride and 0.1% EDTA as preservatives.

Acute intranasal administration of this midazolam formulation in healthy volunteers (100-160 µl into each nostril) is associated with mild to moderate transient irritation of the nasal mucosa (Gudmundsdottir et al., 2001).

A further disadvantage associated with this formulation is that the preservative mixture of 0.02% benzalkonium chloride/0.1% EDTA inhibits the ciliary movement in vitro and is classified as ciliostatic (Merkus et al., 2001). Also the use of the high Captisol® concentration (14%) required to solublize midazolam will also lead to a strong ciliostatic effect.

It is known that ciliary beating is the major factor in normal functioning of the nasal mucociliary clearance, which is a very important defence mechanism of the respiratory tract (Marttin et al., 1998). Nasal administration of the midazolam formulation of Loftsson et al. (2001) can therefore be expected to disturb the mucociliary clearance of the patients. More importantly, the midazolam concentration of this nasal formulation is too low to provide adequate therapeutic efficacy of the drug.

The intranasal midazolam formulation used by Knoester et al. (2002a, 2002) and Tenk et al. (2003) consists of midazolam hydrochloride (30.9 mg/ml) in a mixture of 25% (v/v) propylene glycol and water (pH 4). It also contains 1% (v/v) benzyl alcohol as a preservative. A dose of 5 mg midazolam base is delivered by two sprays of 90 µl and, for a dose of 10 mg midazolam base, 4 sprays of 90 µl are needed (providing a total dose of 360 µl).

The use of this formulation for intranasal midazolam administration in healthy volunteers and in epilepsy patients, providing a dose of 5 mg or 10 mg (90-180 µl in each nostril), causes nasal irritation, lacrimation and irritation of the throat in almost all subjects, as well as a bitter taste (Knoester et al., 2002; Tenk et al., 2003). In in vitro experiments with ciliated tissue, this midazolam formulation has been shown to be ciliostatic, probably due, in particular, to the presence of 25% propylene glycol and 1% benzyl alcohol (Merkus et al., 2001). It is evident from these studies that the volume of the formulation used to administer a dose of 5 and 10 mg via the nose is very large (two and four nasal sprays), and this is probably the cause of many of these adverse side effects. These adverse effects could prohibit the use of this formulation in clinical practice.

SUMMARY OF THE INVENTION

In light of the foregoing, it is clear that there is the need for a midazolam formulation which is specifically formulated for intranasal administration, in order to overcome all of the various disadvantages associated with the known formulations which are administered intranasally. It is therefore an aim of the present invention to provide a formulation with a high enough midazolam concentration to allow adequate doses of midazolam to be efficiently and comfortably administered via the intranasal route in a small volume. The formulation should also cause as little irritation as possible and have as high a bioavailability as possible. Finally, the formulation should have a similar or reduced ciliostatic effect in in vitro experiments, compared to the known nasal formulations.

These and other objects of the invention are achieved by providing a pharmaceutical composition which comprises a solution of high concentration midazolam and a solubilizer. The composition is preferably provided in the form of an aqueous solution and preferably administered intranasally. Such composition can be administered to patients in the treatment of anxiety, epilepsy and epileptic seizures, invasive surgical procedures and diagnostic procedures and sedation.

DETAILED DESCRIPTION OF THE INVENTION

According to a first aspect of the present invention, a pharmaceutical composition is provided, wherein the composition is a solution comprising midazolam in a concentration of at least 35 mg/ml (based on the free base form of midazolam), and a solubilizer. The composition may contain midazolam either in the form of its free base or a pharmaceutically acceptable salt thereof.

The compositions according to the present invention are preferably suitable for intranasal administration.

In one embodiment of the invention, the concentration of midazolam is at least 40 mg/ml, or at least 50 mg/ml. The midazolam concentration may also be less than 100 mg/ml, less than 75 mg/ml or less than 60 mg/ml. In a preferred embodiment, the midazolam concentration is 35-75 mg/ml.

In a particularly preferred embodiment of the present invention, the composition is an aqueous solution. The aqueous solutions of the present invention containing high midazolam concentrations are facilitated by the inclusion in the solution of a solubilizer. Particularly effective solubilizers include propylene glycol, glycerol, polyethylene glycol, povidone and ethanol, or combinations thereof. The inclusion of solubilizers not only enables the formation of an aqueous midazolam solution, but also allows that solution to have a high midazolam concentration. The preferred solubilizers for inclusion in the compositions of the present invention are discussed in greater detail below.

The prior art does not disclose nasal midazolam formulations having such high midazolam concentrations. The reason for this is that it was previously considered that the limited solubility of midazolam meant that concentrations of up to around 30 mg/ml was the maximum possible (see Table 1). However, this is not true, especially when using propylene glycol alone as the solubilizer or propylene glycol in combination with glycerol and optionally one or more of polyethylene glycol, povidone, and ethanol; and water. It was also considered in the prior art that the formulations for nasal administration should have a pH of no less than about 4, as the intranasal administration of a formulation with a lower pH was thought to be too uncomfortable, due to irritation. These prejudices have led the skilled person to administer large volumes intranasally, leading to the above discussed problems.

Contrary to the common opinion of the skilled person, the nasal administration of formulations having a pH lower than 4 is not unacceptable to patients. More importantly, the lower pH allows greater amounts of midazolam to be dissolved, allowing composition with higher concentrations of midazolam to be prepared which, in turn, enables smaller volumes of formulation to be administered.

The high midazolam concentration has a number of surprising advantages. Firstly, as discussed above, it means that smaller volumes of the solution can be administered in order to achieve a desired therapeutic effect. This reduces the waste due to varying amounts of the composition being swallowed or dropping out of the nose, so that more of the administered midazolam is properly absorbed and has the desired therapeutic effect. This also reduces the unpleasant taste and irritation which accompanies swallowing of the nasal composition. It also increases the dose consistency and predictability. This, in turn, enables one to achieve a specific therapeutic effect, as the plasma levels achieved following intranasal administration will be predictable and controllable. As discussed below, different midazolam plasma levels result in different therapeutic effects on the patient. The midazolam compositions for intranasal administration disclosed in the prior art do not result in consistent or predictable plasma levels and so do not permit accurate dosing to achieve a specific therapeutic effect.

The high midazolam concentration also means that some therapeutic effects which were previously difficult or impossible to achieve using known midazolam compositions can now be reliably achieved. If one can administer just 50-100 μl per nostril instead of 2, 4 or even 10 times that volume per nostril, this will clearly be beneficial, especially if the patient is nervous or is a crying child or the like. Therefore, in one embodiment of the invention, the composition provides a therapeutically effective dose of midazolam in a total volume of up to about 200 μl. Preferably, the composition provides a therapeutically effective dose of midazolam in a volume of up to about 100 μl, it being possible to administer this dose to each nostril.

Another benefit associated with administering a smaller volume of the composition intranasally is that it results in a smaller area of deposition within the nose. This localised administration within the nose means that any transient irritation will also be localised and limited to a small area within the nose and throat. This, once again, reduces the discomfort experienced by the patient.

Additionally, the high midazolam concentration has also been demonstrated to enhance diffusion of the active agent through the nasal epithelium, resulting in faster absorption compared to that observed with solutions having lower midazolam concentrations. This not only means a faster onset of the therapeutic effect, but also a reduction in the time for which the active agent is in contact with the nasal epithelium. Again, this will reduce the patient's discomfort, as the midazolam itself is an irritant. Also, less of the midazolam formulation will reach the throat and so there is less chance for irritation by the formulation ingredients and for experiencing the bitter taste of midazolam.

In one embodiment of the invention, the midazolam included in the composition is a salt of midazolam, such as midazolam hydrochloride, midazolam maleate or midazolam lactate. Preferably, the composition comprises midazolam hydrochloride.

In a preferred embodiment of the invention, the solubilizer comprises propylene glycol. Propylene glycol is a good solubilizer for midazolam including salts thereof, e.g. HCl, especially when the midazolam is to be formulated as an aqueous solution. In addition to the propylene glycol, the solubilizer may further comprise one or more of the following: glycerol, polyethylene glycol, povidone, and ethanol. Water is included in the formulation of the preferred solutions.

In an alternative embodiment of the invention, the solubilizer comprises glycerol, another good solubilizer for midazolam when an aqueous solution is to be formed. In addition to the glycerol, the solubilizer may further comprise one or more of the following: propylene glycol, polyethylene glycol, povidone, and ethanol. Water is included in the formulation of the preferred solutions.

In a particularly preferred embodiment of the invention, the composition is a solution of midazolam comprising 90-10%, 80-20%. 70-30%, 60-40% or 40-50% (v/v) solubilizer, preferably propylene glycol. The composition preferably also comprises 10-90%, 20-80%, 30-70%, 40-60% or 50-60% (v/v) water. Furthermore, the composition preferably comprises 40-75 mg/ml midazolam. A composition comprising 40-50% (v/v) propylene glycol and 50-60% (v/v) water is considered as being particularly advantageous.

In one embodiment of the invention, the composition comprises a combination of propylene glycol and glycerol. Glycerol has a sweet taste and, in addition to acting as an excellent solubilizer, it also serves to mask the taste of the midazolam, should some of the solution go down the back of the throat of the patient.

Propylene glycol and glycerol have further advantages. Compositions comprising solubilizers containing propylene glycol (>15% v/v) and/or glycerol (>20% v/v) do not need to include a preservative, because it is known from the literature that these concentrations of glycerol and of propylene glycol act as antimicrobial preservatives (Handbook of Pharmaceutical Excipients, Third Edition, The Pharmaceutical Press, London 2000).

Propylene glycol, glycerol, polyethylene glycol and povidone are also attractive solubilizers for use in a nasal solution because they do not have a strong adverse effect on ciliary movement. In in vitro experiments, according to a previously published method (Merkus et al, 2001), the effect of four different solubilizers [25% propylene glycol, 15% glycerol, 25% polyethylene glycol 400 and 5% povidone], dissolved in a Locke-Ringer solution, on the ciliary beat frequency (CBF) of ciliated tissue taken from chicken embryo tracheal tissue was measured.

All four compounds showed a decrease in CBF after 15 minutes. However, after rinsing with Locke-Ringer solution, the effects on CBF appeared to be completely reversed within 20 minutes.

The solubilizers used in the compositions of the present invention should cause as little irritation as possible when administered in vivo, and preferably no irritation at all. While transient and mild irritation can be tolerated by patients, this should be kept to a minimum in order to avoid unnecessary discomfort.

The preferred solubilizers used in the present invention and discussed above will not cause unnecessary irritation upon intranasal administration.

Despite the reduction in the amount of swallowed composition achieved by using the compositions of the present invention, it is nevertheless possible that a very small part of the midazolam dose will reach the throat, which may lead to a bitter taste. Therefore, in another embodiment of the invention, one or more sweeteners are included in the composition, to mask the bitter taste of midazolam. According to this embodiment, the formulation may comprise midazolam in a concentration of at least 35 mg/ml, a solubilizer and a sweetener.

Suitable sweeteners for inclusion in the compositions of the present invention include saccharin and saccharin alkali salts (which may be included in an amount of about 0.1-5% w/v), aspartame (which may be included in an amount of about 0.1-5% w/v), acesulfame K and cyclamate.

Further additional components which may be included in the compositions of the present invention include flavouring agents, preservatives, buffers, stabilising agents and pH adjusting agents, known from the pharmaceutical literature (Martindale 33rd edition, The Pharmaceutical Press, London 2002). In a preferred embodiment, the composition is free from any buffers.

Suitable flavouring agents include vanilla (vanillin), mint, raspberry, orange, lemon, grapefruit, caramel, cherry flavours and combinations of these.

Suitable stabilizing agents include cyclodextrins such as beta-cyclodextrin (which may be included in an amount of about 1%) and derivatives of beta-cyclodextrin (which may be included in an amount of about 1-4%).

In an alternative embodiment, the compositions according to the present invention are free from any preservatives and/or stabilising agents. In another embodiment, the composition is free from benzyl alcohol In a yet another embodiment of the invention, the compositions further comprise a viscosity enhancing agent. Viscosity enhancing agents are well known to the person skilled in the art from the pharmaceutical literature and will include agents such as cellulose derivatives. Enhancing the viscosity of the solution can enhance the delivery of the midazolam. Viscosity enhancing agents such as cellulose derivatives may also serve to increase the stability of the solutions.

The enhanced absorption of midazolam using the compositions according to the present invention means that the compositions of the invention may be free from any absorption enhancers.

The pH of the composition is preferably within the range of 2.5 to 7. In one embodiment, the pH of the composition is less than 4, and is preferably greater than 2.5. More preferably, the pH of the composition is between 3 and 4. Particularly preferably, the pH is about 3; and most preferably 3.2 Despite there being a general prejudice against compositions for nasal administration having such a low pH value, it has been found that there are no adverse effects or disadvantages associated with a composition having a pH in this range. Indeed, the midazolam is more soluble at lower pHs, making it easier to formulate solutions with high midazolam concentrations.

A pharmaceutically acceptable acid may be added to the solution in order to adjust the pH.

The free midazolam base is rather lipophilic with a partition coefficient between octanol and phosphate buffer (pH 7.5) of about 475. Therefore, the aqueous solubility of the midazolam base at neutral pH is too low to prepare suitable midazolam formulations and for this purpose midazolam salts (e.g., with hydrochloride) have to be used. Ionization of a drug will increase its aqueous solubility. In acidic solutions, midazolam as well as other 1,4-benzodiazepines are known to undergo reversible and pH-dependent ring-opening through the formation of aldehyde or ketone and a primary amine (Gerecke, 1983; Olivier et al, 2001; Loftsson et al., 2001). In the commercially available intravenous solutions of midazolam (5 mg/ml) with a pH of 3.3 to 3.5 the drug consists of 80-85% in the ring-closed form and 15-20% in the ring-open form (Gerecke, 1983).

In this solution the ring-open form is considered as a prodrug of midazolam, because the ring is completely closed when the pH is increased to 7.4.

Intranasal administration of midazolam is characterized by rapid midazolam absorption, reaching maximum plasma concentrations in 5-15 minutes. The drug is subsequently eliminated from the blood circulation with half-lives ranging between 1 and 2.4 hours in children and healthy adults, which are not substantially different from that after intravenous injection of midazolam (Rey et al., 1991; Björkman et al., 1997; Burstein et al., 1997; Loftsson et al., 2001; Knoester et al., 2002; Tenk 2003).

Using the available midazolam injection solutions for intranasal midazolam delivery in children, healthy volunteers and adult surgical patients, mean absolute bioavailabilities of 50, 55 and 83% respectively, have been reported (Rey et al., 1991; Burstein et al., 1991; Björkman et al., 1997).

Examples of compositions according to the present invention are set out below.

EXAMPLE 1

Midazolam HCl 35-75 mg/ml (i.e., 35-75 mg/ml midazolam free base)
Propylene glycol q.s. (in an amount sufficient to solubilize midazolam)
Water Optionally, one or more of the following additional components may be added: polyethylene glycol, glycerol, povidone, ethanol, sweetener, flavouring substance, preservative, pH adjusting agent and stabilizing agents.

This composition is preferably formulated as a nasal spray or nasal drops or liquid for children and adults with a volume of 50-100 µl, for intranasal administration.

The composition has a pH of between 2.5 and 7, preferably between 3 and 4.

EXAMPLE 2

Midazolam HCl 35-75 mg/ml (i.e., 35-75 mg/ml midazolam free base)
Propylene glycol 5-50% (v/v)
Glycerol 5-50% (v/v)
Polyethylene glycol 5-50% (v/v)
Povidone 1-20% (w/v)
Water The composition is formulated as a nasal spray or nasal drops or liquid with a volume for children and adults of 50-100 µl.

The pH of the solution should be between 2.5 and 7, preferably between 3 and 4.

EXAMPLE 3

Midazolam HCl 35, 40, 45 or 50 mg/ml, respectively, (i.e. 35, 40, 45 or 50 mg/ml midazolam free base)
Propylene glycol 15-30% (v/v)
Glycerol 15%-30% (v/v)
Saccharin sodium 10-50 mg/ml
Water The volume for intranasal administration is 50-100 µl.

The pH of the solution should be between 2.5 and 7, preferably between 3 and 4.

EXAMPLE 4

Midazolam HCl 35, 40, 45 or 50 mg/ml, respectively, (i.e., 35, 40, 45 or 50 mg/ml midazolam free base)
Propylene glycol 20-50% (v/v)
Povidone 1-10% (w/v)
Water The volume for nasal administration is 50-100 µl.

The pH of the solution should be between 2.5 and 7, preferably between 3 and 4.

EXAMPLE 5

The following constituents were mixed together to form an aqueous solution of the present invention.
Midazolam HCl 50 mg/ml (i.e., 50 mg/ml midazolam free base)
45% (v/v) Propylene glycol
55% (v/v) Water
The pH of this solution was adjusted to 3.

The intranasal midazolam solutions according to the present invention, providing to the subject a dose of 0.2 mg/kg bodyweight is an interesting new route of drug administration.

According to a second aspect of the present invention, the compositions according to the first aspect may be used in the following situations:
1) as sedative and anxiolytic agents for children undergoing diagnostic and surgical procedures;
2) as sedative and anxiolytic agents for adults undergoing gastrointestinal endoscopy and other diagnostic procedures;
3) as treatment of acute epileptic and febrile seizures in children in medical centres and at home; and
4) as acute management to treat seizures in adults with severe epilepsy in medical centres and at home.

Conscious sedation using intranasal midazolam is a particularly attractive pre-operative technique which avoids the dangers and inconvenience of general anaesthesia in children and adults alike. Also, the use of midazolam in epilepsy sufferers is well documented in many clinical studies.

A good correlation between plasma levels and pharmacodynamic responses has been established for midazolam in a clinical study in which patients, undergoing abdominal surgery, received an intravenous midazolam infusion (Persson et al., 1988). The results are summarized as follows: (1) midazolam plasma concentrations from 75 ng/ml to a range of 150 to 200 ng/ml are able to induce pronounced sedation and partial amnesia; (2) at plasma concentrations of 150 to 200 ng/ml the sleeping patients are arousable; and (3) midazolam plasma levels of 250 to 300 ng/ml are required to achieve satisfactory hypnotic effects during surgery. From many publications it is also evident that the plasma threshold concentration of midazolam for the induction of conscious sedation is in the order of 40 to 50 ng/ml (Allonen et al., 1981; Crevoisier et al., 1983; Persson et al., 1988).

Intranasal delivery of midazolam at dosages of 0.2 to 0.25 mg/kg body weight can reach mean peak plasma concentrations ranging from 100 to 185 ng/ml in children and adults (Rey et al., 1991; Malinovsky et al., 1993; Burstein et al., 1997). In these clinical studies therapeutically effective plasma concentrations of midazolam are manifest as rapidly as 3 minutes after nasal administration and are maintained for about 1 hour. This relationship between plasma levels and clinical effect of midazolam is derived from nasal delivery studies using the commercial midazolam injection solution, and is also valid for nasal administration of midazolam in more concentrated solutions. For example, Tenk et al. (2003) administered midazolam intranasally in epilepsy patients at dosages of 5 and 10 mg/patient (equivalent to about 0.06 and 0.12 mg/kg, respectively), using the midazolam formulation of Knoester et al. (2002a, 2002). Maximum plasma concentrations of 73 and 140 ng/ml are reached in 5 to 10 minutes, and for both nasal midazolam dosages the sedative effects in the patients last for 45 to 60 minutes after administration.

A clear relationship between plasma midazolam concentrations and its clinical effect is not always well established. Gudmundsdottir et al. (2001) did a pharmacokinetic/pharmacodynamic study in healthy volunteers after nasal delivery of midazolam (0.06 mg/kg; 100-160 µl into each nostril), using the midazolam formulation of Loftsson et al. (2001). Low mean peak serum levels of 42 ng/ml within 10-15 minutes are observed, which are in the range of the reported threshold concentration for induction of sedation. Some sedative activity in the volunteers is shown for 1 hour after nasal administration. As stated before, the midazolam concentration used in the Loftsson formulation is not high enough to achieve optimal clinical effects.

The above mentioned plasma levels of midazolam are achieved by intranasal administration of the composition of the present invention, the dose of midazolam being selected to provide the plasma level which will result in the desired therapeutic effect. Preferably, the desired midazolam plasma level is achieved within 3 to 15 minutes of nasal administration of the composition.

The compositions of the present invention are preferably formulated for spray delivery, for example, by a pump spray device. Suitable devices which are already commercially available include multiple dose vials and bi-dose or unit-dose devices. The preferred devices are unit-dose devices and bi-dose devices. It is also possible to use disposable plastic unit-dose containers manufactured, for instance, by blow-fill-seal technology and known from commercial eye drops, to deliver a small volume of an intranasal midazolam formulation as a nasal liquid or nasal drops.

The compositions of the present invention can also be administered in a liquid, semi-liquid, or semi-solid formulation for sublingual, buccal, rectal or any other transmucosal administration using a tampon, sponge, rectal or oromucosal capsule (i.e. a capsule for oromucosal absorption, such as buccal or sublingual mucosal absorption), mucosal patch, chewing gum, lollipop or any other form or device suitable for transmucosal drug delivery known to the skilled person, for example from the pharmaceutical literature.

According to a third aspect of the present invention, a device is provided, for spray delivery or delivery as liquid or nasal drops of a composition according to the first aspect of the present invention. The device preferably holds one or more doses of the composition.

REFERENCES

Allonen H, Ziegler G and Klotz U, Midazolam kinetics. Clin. Pharmacol. Ther. 30: 653-661 (1981).

Björkman S, Rigemar G and Idvall J, Pharmacokinetics of midazolam given as an intranasal spray to adult surgical patients. Br. J. Anaesth. 79: 575-580 (1997).

Burstein A H, Modica R, Hatton M, Forrest A and Gengo F M, Pharmacokinetics and pharmacodynamics of midazolam after intranasal administration. J. Clin. Pharmacol. 37: 711-718 (1997).

Cheng A C K, Intranasal midazolam for rapidly sedating an adult patient. Anesth. Analg. 76: 904 (1993).

Crevoisier Ch, Ziegler W H, Eckert M and Heizmann P, Relationship between plasma concentration and effect of midazolam after oral and intravenous administration. Br. J. Clin. Pharmacol. 16: 51S-61S (1983).

Davis P J, Tome J A, McGowan F X, Cohen I T, Latta K and Felder H, Preanesthetic medication with intranasal midazolam for brief pediatric surgical procedures. Anesthesiology 82: 2-5 (1995).

Gerecke M, Chemical structure and properties of midazolam compared with other benzodiazepines. Br. J. Clin. Pharmacol. 16: 11S-16S (1983).

Gudmundsdottir H, Sigurjonsdottir J F, Masson M, Fjalldal O, Stefansson E and Loftsson T, Intranasal administration of midazolam in a cyclodextrin based formulation: bioavailability and clinical evaluation in humans. Pharmazie 56: 963-966 (2001).

Heizmann P, Eckert M and Ziegler W H, Pharmacokinetics and bioavailability of midazolam in man. Br. J. Clin. Pharmacol. 16: 43S-49S (1983).

Karl H W, Keifer A T, Rosenberger J L, Larach M G and Ruffle J M, Comparison of the safety and efficacy of intranasal midazolam or sufentanil for preinduction of anesthesia in pediatric patients. Anesthesiology 76: 209-215 (1992).

Kendall J, Reynolds M and Goldberg R, Intranasal midazolam in patients with status epilepticus. Ann. Emerg. Med. 29: 415-417 (1997).

Knoester P D, Jonker D M, Van der Hoeven R T M, Vermeij T A C, Edelbroek P M, and De Haan G J, Midazolam intranasaal toegepast, eventueel als noodmedicatie (in Dutch). Pharmaceutisch Weekblad 137: 112-117 (2002a)

Knoester P D, Jonker D M, Van der Hoeven R T M, Vermeij T A C, Edelbroek P M, Brekelmans G J and De Haan G J, Pharmacokinetics and pharmacodynamics of midazolam administered as a concentrated nasal spray. A study in healthy volunteers. Br. J. Clin. Pharmacol. 53: 501-507 (2002).

Kogan A, Katz J, Efrat R and Eidelman L A, Premedication with midazolam in young children: a comparison of four routes of administration. Paediatric Anaesthesia 12: 685-689 (2002).

Lahat E, Goldman M, Barr J, Eshel G and Berkovitch M, Intranasal midazolam for childhood seizures. The Lancet 352: 620 (1998).

Lahat E, Goldman M, Barr J, Bistritzer T and Berkovitch M, Comparison of intranasal midazolam with intravenous diazepam for treating febrile seizures in children: prospective randomised study. Br. Med. J. 321: 83-86 (2000).

Loftsson T, Gudmundsdottir H, Sigurjonsdottir F J, Sigurosson H H, Sigfusson S D, Masson M and Stefansson E, Cyclodextrin solubilization of benzodiazepines: formulation of midazolam nasal spray. Int. J. Pharm. 212: 29-40 (2001).

Lugo R A, Fishbein M, Nahata M C and Lininger B, Complication of intranasal midazolam. Pediatrics 92: 638 (1993).

Lui C Y, Amidon G L and Goldberg A, Intranasal absorption of flurazepam, midazolam and triazolam in dogs. J. Pharm. Sci. 80: 1125-1129 (1991).

Malinovsky J M, Lejus C, Servin F, Lepage J Y, Le Normand Y, Testa S, Cozian A and Pinaud M, Plasma concentrations after i.v., nasal or rectal administration in children. Br. J. Anaesth. 70: 617-620 (1993).

Malinovsky J M, Populaire C, Cozian A, Lepage J Y, Lejus C and Pinaud M, Premedication with midazolam in children. Effect of intranasal, rectal and oral routes on plasma midazolam concentrations. Anaesthesia 50: 351-354 (1995).

Marttin E, Schipper N G, Verhoef J C and Merkus F W H M, Nasal mucociliary clearance as a factor in nasal drug delivery. Adv. Drug Del. Rev. 29: 13-38 (1998).

Merkus P, Romeijn S G, Verhoef J C and Merkus F W H M, Classification of cilio inhibiting effects of nasal drugs. Laryngoscope 111: 595-602 (2001).

Olivier J C, Djilani M, Fahmy S and Couet W, In situ nasal absorption of midazolam in rats. Int. J. Pharm. 213: 187-192 (2001).

O'Regan M E, Brown J K and Clarke M, Nasal rather than rectal benzodiazepines in the management of acute childhood seizures? Develop. Med. Child Neurol. 38: 1037-1045 (1996).

Payne K, Mattheyse F J, Liebenbenberg D and Dawes T, The pharmacokinetics of midazolam in paediatric patients. Eur. J. Clin. Pharmacol. 37: 267-272 (1989).

Persson M P, Nilsson A and Hartvig P, Relation of sedation and amnesia to plasma concentrations of midazolam in surgical patients. Clin. Pharmacol. Ther. 43: 324-331 (1988).

Randell T T and Kyttä, Conscious sedation in patients undergoing surgical and investigational procedures. A guide to drug choice. CNS Drugs 10: 329-342 (1998).

Rey E, Delaunay L, Pons G, Murat I, Richard M O, Saint-Maurice C and Olive G, Pharmacokinetics of midazolam in children: comparative study of intranasal and intravenous administration. Eur. J. Clin. Pharmacol. 41: 355-357 (1991).

Saint-Maurice C, Meistelman C, Rey E, Esteve C, De Lauture D and Olive G, The pharmacokinetics of rectal midazolam for premedication in children. Anesthesiology 65: 536-538 (1986).

Scheepers M, Scheepers B, Clarke M, Comish S and Ibitoye M, Is intranasal midazolam an effective rescue medication in adolescents and adults with severe epilepsy? Seizure 9: 417-422 (2000).

Smith M T, Eadie M J and O'Rourke Brophy T, The pharmacokinetics of midazolam in man. Eur. J. Clin. Pharmacol. 19: 271-278 (1981).

Taylor M B, Vine P R and Hatch D J, Intramuscular midazolam premedication in young children. Anaesthesia 41: 21-26 (1986).

Tenk H, Jonker D M, Van der Hoeven R T M, Vermeij T A C, Edelbroek P M and De Haan G J, Midazolam neusspray bij patiënten met epilepsie. Pharm. Weekbl. 138: 99-103 (2003).

Theroux M C, West D W, Corddry D H, Hyde P M, Bachrach S J, Croman K M and Kettrick R G, Efficacy of intranasal midazolam in facilitating suturing of lacerations in preschool children in the emergency department. Pediatrics 91: 624-627 (1993).

Tolle-Sander S, Rautio J, Wring S, Polli J W and Polli J E, Midazolam exhibits characteristics of a highly permeable P-glycoprotein substrate. Pharm. Res. 20: 757-764 (2003).

Uygur-Bayramicli O, Dabak R, Kuzucuoglu T and Kavakli B, Sedation with intranasal midazolam in adults undergoing upper gastrointestinal endoscopy. J. Clin. Gastroenterol. 35: 133-137 (2002).

Walbergh E J, Wills R J and Eckhert J, Plasma concentrations of midazolam following intranasal administration. Anesthesiology 74: 233-235 (1991).

Wilton N C T, Leigh J, Rosen D R and Pandit U A, Preanesthetic sedation of preschool children using intranasal midazolam. Anesthesiology 69: 972-975 (1988).

The invention claimed is:

1. A method of inducing sedation, anxiolysis, or anesthesia in a patient in need thereof comprising administering an effective amount of a pharmaceutical composition for intranasal administration, comprising an aqueous solution of midazolam in a concentration of from 35 mg/ml to 100 mg/ml; a solubilizer comprising at least one of propylene glycol, glycerol, polyethylene glycol, povidone, or ethanol; and water, the composition having a pH greater than 2.5 and less than 4.

2. The method of claim 1, wherein the patient is undergoing invasive surgical procedures.

3. A method of treating a patient suffering from epilepsy comprising administering an effective amount of a pharmaceutical composition for intranasal administration, comprising an aqueous solution of midazolam in a concentration of from 35 mg/ml to 100 mg/ml; a solubilizer comprising at least one of propylene glycol, glycerol, polyethylene glycol, povidone, or ethanol; and water, the composition having a pH greater than 2.5 and less than 4.

4. The method of claims 1, 2 or 3, wherein the composition is administered in a dose of 50-100 µl per nostril.

5. The method of claims 1, 2 or 3, wherein the composition is administered in a dose of 0.2 mg/kg bodyweight of a patient.

6. The method of claims 1, 2, or 3, wherein the aqueous solution of midazolam has a concentration of midazolam from 40 mg/ml to 100 mg/ml.

7. The method of claims 1, 2, or 3, wherein the aqueous solution of midazolam has a concentration of midazolam is form 50 mg/ml to 100 mg/ml.

8. The method of claims 1, 2, or 3, wherein the aqueous solution of midazolam has a concentration of midazolam from 35 mg/ml to 75 mg/ml.

9. The method of claims 1, 2, or 3, wherein the pharmaceutical composition comprises a pharmaceutically acceptable salt of said midazolam selected from the group consisting of midazolam hydrochloride, midazolam maleate and midazolam lactate.

10. The method of claims 1, 2, or 3, wherein the solubilizer comprises propylene glycol.

11. The method of claims 1, 2, or 3, wherein the solubilizer comprises glycerol.

12. The method of claims 1, 2, or 3, wherein the aqueous solution of midazolam has a concentration of midazolam from 40 mg/ml to 75 mg/ml.

13. The method of claims 1, 2, or 3, wherein the pH of the pharmaceutical composition is adjusted to a pH greater than 3 and less than 4.

14. The method of claims 1, 2, or 3, wherein the pharmaceutical composition comprises a pharmaceutically acceptable acid or base in an amount sufficient to adjust the pH to a value greater than 3 and less than 4.

15. The method of claims 1, 2, or 3, wherein the pharmaceutical composition comprises a spray, nasal liquid or nasal drops.

* * * * *